US008932880B2

(12) United States Patent
Giavazzi et al.

(10) Patent No.: US 8,932,880 B2
(45) Date of Patent: Jan. 13, 2015

(54) METHOD FOR THE DIRECT MEASURE OF MOLECULAR INTERACTIONS BY DETECTION OF LIGHT REFLECTED FROM MULTILAYERED FUNCTIONALIZED DIELECTRICS

(75) Inventors: Fabio Giavazzi, Melegnano (IT); Matteo Salina, Novara (IT)

(73) Assignee: ProXentia s.r.l., Milan (IT)

( * ) Notice: Subject to any disclaimer, the term of this patent is extended or adjusted under 35 U.S.C. 154(b) by 0 days.

(21) Appl. No.: 13/504,592

(22) PCT Filed: Oct. 29, 2010

(86) PCT No.: PCT/EP2010/006613
§ 371 (c)(1),
(2), (4) Date: Jun. 11, 2012

(87) PCT Pub. No.: WO2011/050968
PCT Pub. Date: May 5, 2011

(65) Prior Publication Data
US 2012/0244554 A1 Sep. 27, 2012

(30) Foreign Application Priority Data

Oct. 30, 2009 (IT) .............................. MI2009A1893

(51) Int. Cl.
| G01N 33/551 | (2006.01) |
| B82Y 20/00 | (2011.01) |
| G01N 21/05 | (2006.01) |
| G01N 21/55 | (2014.01) |
| G01N 21/77 | (2006.01) |
| G01N 33/543 | (2006.01) |
| G01N 21/27 | (2006.01) |

(Continued)

(52) U.S. Cl.
CPC ................ *B82Y 20/00* (2013.01); *G01N 21/05* (2013.01); *G01N 21/55* (2013.01); *G01N 21/77* (2013.01); *G01N 33/54313* (2013.01); *G01N 33/54373* (2013.01); *G01N 21/274* (2013.01); *G01N 21/4738* (2013.01); *G01N 2021/7773* (2013.01); *G01N 2021/0346* (2013.01); *Y10S 436/805* (2013.01)
USPC ............ 436/524; 436/164; 436/525; 436/805

(58) Field of Classification Search
None
See application file for complete search history.

(56) References Cited

U.S. PATENT DOCUMENTS 4,558,012 A * 12/1985 Nygren et al. ................ 436/501
4,820,649 A * 4/1989 Kawaguchi et al. .......... 436/501
(Continued)

FOREIGN PATENT DOCUMENTS

| EP | 1792183 B1 | 6/2007 |
| WO | 2007/105081 A2 | 9/2007 |

OTHER PUBLICATIONS

Chen et al., Enhancement of the resolution of surface plasmon resonance biosensors by control of the size and distribution of nanoparticles, Optics Letters, vol. 29, No. 12, Jun. 5, 2004.*

(Continued)

*Primary Examiner* — Chris L Chin
(74) *Attorney, Agent, or Firm* — Young & Thompson

(57) ABSTRACT

Method and apparatus for the quantitative determination of molecular interactions between ligands in solution and receptors immobilized on the surface of a solid transparent material coated by one or more antireflective dielectric layers, through direct measurement of the light reflected by the interface between the surface and the solution.

20 Claims, 5 Drawing Sheets

(51) Int. Cl.
*G01N 21/47* (2006.01)
*G01N 21/03* (2006.01)

(56) References Cited

U.S. PATENT DOCUMENTS

| | | | |
|---|---|---|---|
| 5,313,264 | A | 5/1994 | Ivarsson et al. |
| 5,374,563 | A | 12/1994 | Manule |
| 5,468,606 | A * | 11/1995 | Bogart et al. ............... 435/5 |
| 5,804,453 | A | 9/1998 | Chen |
| 7,319,525 | B2 | 1/2008 | Tan et al. |
| 7,692,798 | B2 | 4/2010 | Striemer et al. |
| 2004/0014060 | A1 | 1/2004 | Hoheisel et al. |
| 2007/0009968 | A1 | 1/2007 | Cunningham et al. |
| 2008/0006815 | A1 | 1/2008 | Wang et al. |

OTHER PUBLICATIONS

Liu et al., Data analysis of surface plasmon resonance biosensor based on phase detection, Sensors and Actuators B, vol. 108, p. 778-783, Feb. 15, 2005.*
Cunningham et al., Colorimetric resonant reflection as a direct biochemical assay technique, Sensors and Actuators B, vol. 81, pp. 316-328, 2002.*
Biow, et al., Optimised film thickness for maximum evanescent field enhancement of a bimetallic film surface plasmon resonance biosensor, Sensors and Actuators B, vol. 114, pp. 1028-1034, Sep. 30, 2005.*
Prosperi D et al.: "Phantom Nanoparticles 1-16 as Probes of Biomolecular Interactions", Small, vol. 2, No. 8-9, Jul. 18, 2006, pp. 1060-1067, XP002585305, online paragraphs [02.1]-[02.4]; figures 2-5 paragraphs [02.7]-[004.], Cited in ISR.
Prosperi Davide et al.: "Avidin decorated core-shell nanoparticles for biorecognition studies by elastic light, scattering", Chembiochem, vol. 8, No. 9, Jun. 2007, pp. 1021-1028, XP002585304, ISSN: 1439-4227 abstract p. 1026; col. 2, line 35-p. 1027, col. 1, Line 22 scheme 1, scheme 2 figures 4-6 p. 1027; col. 2, line 8-last line, Cited in ISR.
Ozkumur M. et al.: "Label-free and dynamic detection of biomolecular interactions for high-throughput microarray applications", PNAS, vol. 105, No. 23, Jun. 10, 2008, pp. 7988-7992, XP002585303, cited in the application p. 7989, col. 2, line 1-p. 7990, col. 1, line 6; figures 1-3, Cited in ISR.
Memisevic J et al.: "Characterization of a novel ultra-low refractive index material for biosensor application", Sensors and Actuators B, Elsevier Sequoia S.A., Lausanne, CH, vol. 141, No. 1, Aug. 18, 2009, pp. 227-232, XP026419834, ISSN: 0925-4005 [retrieved on May 3, 2009] p. 228, col. 1, line 15-col. 2, line 13 paragraphs [03.2]-[004.]; figures 3,4; table 1, Cited in ISR.
Palestino G et al.: "Functionalization of nanostructured porous silicon microcavities for glucose oxidase detection", Sensors and Actuators B, Elsevier Sequoia S.A., Lausanne, CH LNKDDOI: 10.1016/J.SNB.2008.07.013, vol. 135, No. 1, Dec. 10, 2008, pp. 27-34, XP025677089, ISSN: 0925-4005 [retrieved on Jul. 25, 2008] paragraphs [001.]-[02.4] p. 30, col. 1, last paragraph—col. 2, line 4; figure 4 p. 31, col. 1, line 1—p. 32, col. 2, line 11; figures 5-7, Cited in ISR.
Chan L L et al.: "Label-free imaging of cancer cells using photonic crystal biosensors and application to cytotoxicity screening of a natural compound library", Sensors and Actuators B, Elsevier Sequoia S.A., Lausanne, CH LNKD- DOI:10.1016/J.SNB.2007.10.027, vol. 132, No. 2, Jun. 16, 2008, pp. 418-425, XP022707531, ISSN: 0925-4005 [retrieved on Oct. 26, 2007] abstract figures 1-3, Cited in ISR.
Ghetta A. et al.: "Light scattered by model phantom bacteria reveals molecular interactions at their surface", Proceedings of the National Academy of Sciences of the United States-of America, vol. 102, No. 44, Nov. 1, 2005, pp. 15866-15870, XP002585396, ISSN: 0027-8424 p. 102, col. 1, line 23-p. 103, col. 1, line 7; figure 1 figures 3-5, Cited in ISR.
International Search Report, dated Jan. 21, 2011, from corresponding PCT application.

\* cited by examiner

METHOD FOR THE DIRECT MEASURE OF MOLECULAR INTERACTIONS BY DETECTION OF LIGHT REFLECTED FROM MULTILAYERED FUNCTIONALIZED DIELECTRICS

SUMMARY

Herein provided is a method for the quantitative determination of molecular interactions between ligands in solution and receptors immobilized on the surface of a solid transparent material coated by one or more antireflective dielectric layers, with thicknesses and refractive indices such as to reduce the optical reflectivity of the surface, through direct measurement of the light reflected by the interface between said surface and said solution, without the need of labeling moieties. The invention provides also a device for the implementation of the method.

PRIOR ART

In the known art a number of methods has been proposed for the determination of interactions between ligands and receptors, that is the binding affinities and the kinetics of reversible ligand-receptor systems of chemical, biochemical or biological interest. A list of the principal methods is reported in "Biosensors and BioDetection", John M. Walker, Humana Press, 2009. The known methods usually include the immobilization of the receptor on a suitable flat surface and the direct or indirect measurement of the variation of some of the surface properties, optical properties for example, after the solution containing the ligands has been put in contact with the surface. Said variations are induced by the formation of ligand-receptor complexes.

A class of methods requires the labeling of the ligand in solution, that is the covalent modification of the ligand with fluorescent, luminescent of radioactive species (see for example the patent application US 2004/0014060 A1). Nevertheless, it should be noticed that the modification of the ligand typically is a long and complex operation and it can represent a limiting factor, for example in screening essays, where a remarkable variety of ligands is used. Another disadvantage of labeling is that the ligand-receptor interaction may be influenced by the chemical modification of the ligand.

Another class of methods that more effectively mimic the receptor-ligand interactions (such as those occurring on the surface of a cell membrane) exploits the changes in physical properties induced by the formation of a surface receptor-ligand binding, without modifying the ligand with labeling substances. This class of methods is generally called "label-free". An example of these methods is provided by the BIAcore biosensor, marketed by GE Healthcare (Uppsala, Sweden), described for instance in U.S. Pat. No. 5,313,264 and U.S. Pat. No. 5,374,563. In this biosensor, based on the principle of Surface Plasmon Resonance (SPR) (see Article Jiri Homola, Sinclair S. Yee, Gunter Gauglitz, "Surface plasmon resonance sensors: review", Sensors and Actuators B, vol. 54 (1999), pages 3-15) an optical evanescent wave is coupled with the surface plasmon in thin layers (50 nm) of conducting materials such as silver or gold, and generates a resonance phenomenon at specific angles. This allows determining the refractive index of the layer of material immobilized on the metal, such as a ligand-receptor pair, by measuring the angle of minimum reflection. In a common use, from the variation of refractive index versus time the binding constants between ligand and receptor are obtained.

This method, although widely used in practice, is quite complex and expensive and not always accurate in determining the binding constant. See for example the publication "Use of surface plasmon resonance to probe the equilibrium and dynamic interactions Between Aspects of biological macromolecules," Peter Schuck, Annu. Rev. Biophys. Biomol. Struct., 1997, 26, pp. 541-66. The problems associated with the use of the BIAcore method for the determination of binding constants depend largely on the complexity of the method, because the measured signal depends on the physical properties of five materials through a complex functional dependence that includes parameters not known a priori. The five mentioned materials are: substrate of glass or similar materials, thin conductive film, biocompatible polymer layer, receptor, molecules that adhere though the interaction and aqueous solution.

Said problems produce:

1) the disagreement between the affinity constant values determined through the binding kinetics and those obtained at the thermodynamic equilibrium;

2) the impossibility to predict the intensity of the signal generated when ligand/receptor couples are formed on the surface, since the signal depends on parameters that are not previously known.

Another family of label-free methods (commonly referred to as reflectometric interference spectroscopy) is based on the measure of the spectral shift of the light reflected by a transparent substrate such as glass or quartz, presenting a surface coated with a thin layer (with a thickness comprised between a fraction of a micron and a few tens of microns) of dielectric material such as silicon dioxide or polystyrene. The substrate may take the form of a flat plate, as in the case of the so-called Microcuvette Fabry-Perot interferometer-based biosensors (see for example the publication of A. Brecht, J. Ingenhoff, G. Gauglitz, "Direct monitoring of antigen-antibody interactions by spectral interferometry", Sensors and actuators B: Chemical, Vol 6, pp. 96-100 (1992)), or it can be shaped in the form of fiber, with one end made plain and smooth (see for example patent applications U.S. Pat. No. 5,804,453 and U.S. Pat. No. 7,319,525). Said surface, on which are immobilized by various techniques molecules with the function of receptor, is placed in contact with the solution where the analytes of interest are present. The surface is illuminated with polychromatic light and the reflected light is collected and sent to a spectrometer. The thickness of the dielectric layer is apt to introduce a modulation in the spectrum of reflected light, with several interference maxima and minima. The position of the interference maxima and minima is uniquely determined by the thickness of the dielectric layer and its refractive index. The adhesion of ligand molecules on the surface changes the spectrum of reflected light and, in particular, produces a shift in the position of the interference maxima and minima. By measuring these changes in the spectrum of reflected light it is possible to determine the thickness of the molecular layer on the surface. As an example of instrument based on this principle we cite the Octect marketed by Fortebio (Menlo Park, Calif. 94025 USA).

A variant of the described method based on the measure of the changes of the spectrum of reflected light is discussed in the recent publication of E. Ozkumur, J. W. Needham, D. A. Bergstein, R. Gonzalez, M. Cabodi, J. M. Gershon, B. B. Goldberg, M. S. Unlu., "Label-free and dynamic detection of Biomolecular interactions for high-throughput microarray applications," PNAS, Vol 105, pp. 7988-7992 (2008). In this case on the sensor surface, consisting of a flat plate of silicon coated with a thin layer of silicon dioxide, different receptors are immobilized in different circular regions and the measurement of the changes introduced in the spectrum of light reflected by the adhesion of ligand molecules on the surface occurs in a spatially resolved way. The surface is illuminated sequentially with a series of monochromatic light beams (from a tunable laser), with evenly spaced wavelengths and, for each lighting condition, a reflection image of the surface is recorded by a digital camera. The sequence of the intensity values recorded by each element (pixel) of the camera allows the reconstruction of a portion of the spectrum of light reflected from the corresponding region on the sensor surface. In this way, the spectral changes caused by the adhesion of the ligands can be measured separately for each of the regions the surface is divided into.

The methods in this family, based on the measure of the spectrum of reflected light, while based on different physical principles than the methods based on the principle of SPR, like the latter are rather complex and expensive to implement, requiring the use of a spectrometer or a variable wavelength monochromatic light source (such as a tunable laser). A different detection method based on the use of a substrate formed by a layer of silicon dioxide on a silicon wafer is described in (US patents 2008/006815 and U.S. Pat. No. 7,692,798). In this method, the detection of the amount of ligand molecules interacting with the receptors immobilized on the surface is based on the measure of the intensity of reflected light. Although this approach is in principle simpler then the methods above because it does not require the use of a spectrometer, its use is limited by few problems due to the specificity of silicon. Because of its high refractive index, the measure does not take place in aqueous environment and the detection is limited to a very narrow angle of reflection, thus increasing the complexity of the instrument and limiting its use with fluid samples. Moreover, since the silicon substrate is not transparent to the visible light, this method is not suitable to be combined with other methods requiring transparent substrates.

Another class of methods for the measure of ligand-receptor interactions is based on the use of suspended nanoparticles with functionalized surface. Among this class, a label-free method based on the use of suspended nanoparticles made of amorphous perfluorinated polymer having refractive index close to that of water has been recently proposed (EP1792183 and the publications Davide Prosperi, Carlo Morasso, Francesco Mantegazza, Marco Buscaglia, Loren Hough, Tommaso Bellini, "Phantom Nanoparticles as Probes of Biomolecular Interactions", Small, Vol. 2, pp 1060-1067 (2006) and Davide Prosperi, Carlo Morasso, Paolo Tortora, Diego Monti and Tommaso Bellini, "Avidin Decorated Core-Shell Nanoparticles for Biorecognition Studies by Elastic Light Scattering, ChemBioChem, Vol. 8, Issue 9, pp 1021-1028 (2007)). In said method, the detection of the interaction between ligands in solution and receptors immobilized on the surface of the suspended nanoparticles is based on the change of the intensity of the light scattered in every direction when the interaction takes place. Said method overcomes some of the limitations of other label-free methods, facilitating the measurement at thermodynamic equilibrium, which is reached in a very short time because of the free diffusion of the nanoparticles in solution. Nevertheless, said method does not allow the measure of many common interactions, in which the ligands are multivalent, since in this case the interaction with the receptor immobilized on the surface of the nanoparticles can induce their aggregation, thus affecting the measure of the intensity of the scattered light and complicating the interpretation of the detected signal in terms of ligand-receptor interaction.

An alternative method recently proposed for the determination of interactions between ligands and receptors without the need for labeling and allowing the use of multivalent ligands is based on the measurement of light reflected from an interface between an aqueous fluid and an extended solid material made of perfluoropolymers with a refractive index very close to it (patent PCT/IB2007/000618). In this method, the amount of molecules in solution adhering to the interface, where the molecules with function of receptor are immobilized, is derived directly from the increase of the intensity of light undergoing specular reflection from the functionalized planar surface.

Although this method can be implemented using low cost light sources and detectors (eg, LED and photodiode), the main disadvantages of the method are due to the high cost of perfluorinated polymer used as a substrate and the absence of a known process for the receptor immobilization by chemical bonding to the surface of that material, characterized by a very low reactivity, as many fluorinated compounds.

The need was therefore felt to have available a simple method for the determination of interactions between ligands and receptors directly exploiting the variations induced by the ligand-receptor interaction on a surface, avoiding the ligand labeling operations, allowing the determination of the affinity constant values under thermodynamic equilibrium conditions, thus avoiding the drawbacks of the indirect methods, such as, for example, BIAcore, and allowing the use of the method also in the study of multivalent ligands, since most of the ligands of biological and pharmacological interest have multiple binding sites. In particular, the need was felt for a high sensitivity method, whose signal was detectable by means of instrumentation simple to build, and was quantitatively interpretable through previously known parameters, overcoming, in this way, the prior art drawbacks.

DESCRIPTION OF THE INVENTION

The present invention allows the attainment of these objectives, avoiding the aforementioned disadvantages encountered with known techniques, through an optical method that allows quantitative detection of an analyte in solution and its concentration by the procedure described below.

It is known that the reflectivity associated with the interface between two different media can be greatly reduced by the presence, on the surface of one of the two media (substrate), of one or more dielectric layers, each one with a thickness of tens or hundreds of nanometers, superimposed each others. These layers form a so called antireflective coating.

It is now found that by using a substrate coated by dielectric layers such that the reflectivity of the surface is less than 0.01%, preferably less than 0.001%, when put in contact with an aqueous medium, on the surface of said substrate molecules being immobilized with the function of receptor, and an apparatus to measure the intensity of light reflected from the interface between the multilayered surface and an aqueous solution, when at the interface molecules accumulate to form aggregates or molecular layers, it is possible to determine the total mass of the molecules bound at the interface with the aqueous solution by measuring the intensity of the reflected light.

It is therefore object of the present invention a method for determining the presence of a ligand in solution, its quantity, concentration, binding affinity, kinetic constants of association and/or dissociation of the ligand itself with its receptor, using measurements of intensity of reflected light, comprising the following steps:

a) prepare a substrate of a solid crystalline or amorphous material with a smooth planar surface covered by one or more dielectric layers of thickness comprised between 50 nm and 500 nm, so that the reflectivity of that surface, in contact with an aqueous solution is less than 0.01%;

b) immobilize the receptor molecules on said surface;

c) bring into contact said surface coated by receptor molecules with the solution containing the ligand;

d) measure the intensity of light reflected from the interface between the solution and the surface coated by receptor molecules as a function of time, converting the intensity values of reflected light in mass per unit area of ligand molecules interacting with the immobilized receptors using the Fresnel formulas.

Preferably, the substrate of solid material and said dielectric layers have refractive index, respectively, between 1.4 and 1.7 and between 1.35 and 1.65. In addition, the substrate is preferably made of siliceous glass.

In a realization, the value of intensity of reflected light or the value of mass per unit area of ligand molecules interacting with the immobilized receptors, as measured in step d), are converted into total amount or concentration of ligand molecules present in solution.

In a further implementation, the value of the intensity of reflected light or the value of mass per unit area of ligand molecules interacting with the immobilized receptors, as measured in step d), are converted into the affinity constant of ligand-receptor couple.

In a further implementation, the values of the intensity of reflected light as a function of time measured in step d) are converted into the kinetic constants of association and/or dissociation of ligand-receptor couple.

In a further implementation, the low reflectivity surface obtained through the steps a) and b) is divided into different regions, possibly arranged in a matrix. In different regions different receptors are adsorbed or immobilized and the intensity of the light reflected from different regions is measured simultaneously through an imaging system.

On the surface coated by receptors other molecules (spacers) that have no function of the receptor can be immobilized. In addition, the low-reflective surface may be included either in a cell for measurements in the absence of flow in a flow cell, or in an immersion probe.

According to the present invention, the receptors and ligands are selected from proteins, peptides, nucleic acids, glycoproteins, carbohydrates, hormones, lipids, cells, or cellular components, viruses or molecules of pharmacological interest. Receptors can be immobilized on the surface through:

chemical bonding;
adsorption;
adsorption on molecules or polymers in turn immobilized on the surface;
electromagnetic radiation;
plasma treatment.

The solution containing the ligands and brought into contact with the surface of the material may be an aqueous solution or it can contain organic solvents, possibly mixed with water.

The angle of incidence, the polarization, the angular divergence and the spectral properties of the incident light are selected in order to optimize the ratio between the reflected light signal in the presence of receptor-ligand interaction and the background noise due to spurious reflection and scattering.

Another aspect of the invention concerns a device for the implementation of the method described here, which includes at least one cell apt to contain the solution with the ligand and to make the ligand-receptor reaction take place, means allowing the flow of the solution respectively to and from the cell, a source and a light detector equipped with means for measuring the intensity of light emitted respectively incident and reflected, and possibly one or more mirrors, lenses and apertures.

In a preferred embodiment, the light source is an LED light source and said detector is a CCD (Charged Coupled Device) or CMOS (Complementary Metal-Oxide Semiconductor).

DETAILED DESCRIPTION OF THE INVENTION

Through the method of the invention, measuring the intensity of the reflected light it is possible to determine the total mass of the molecules present at the interface with the solution, as described in the following.

From the values of intensity of reflected light are obtained the corresponding mass values of molecules with the function of ligand coated on the different regions of the surface by the formula:

$$I_R = RI_0 + I_B \quad (1)$$

where:

$I_0$ represents the intensity of light incident on the interface $I_B$ is the intensity of light measured by the detector in the absence of the interface R is the reflection coefficient (i.e. the reflectivity) obtained from the Fresnel formulas for stratified dielectric media, depending on the amount of ligand in contact at any given time with the receptors immobilized on the surface. The Fresnel formulae for stratified dielectric media may be for example those reported in, Max Born and Emil Wolf, Cambridge University Press, Cambridge, United Kingdom, 1999, pages 59-70.

As an example we consider the case of a substrate of refractive index $n_0$ coated by a single dielectric layer of refractive index $n_1$, comprised between $n_0$ and the refractive index $n_3$ of the solution in contact with the dielectric layer. In this condition it is known that the layer itself may have anti-reflection function, decreasing the reflectivity of the substrate-solution interface. In the case of illumination with collimated light, monochromatic with wavelength $\lambda$, incident on the surface, the decrease of reflectivity is more pronounced as the thickness h of the dielectric layer is close to the value $\lambda/(4n_1)$ and the more the combination $n_0 n_3 / n_1^2$ is close to 1. For example, for the following parameters values:

$\lambda = 632.8$ nm (He—Ne laser)
$n_0 = 1587 \pm 0005$ (Schott glass N-SK5)
$n_1 = 1457 \pm 0005$ (amorphous $SiO_2$)
$n_3 = 1334 \pm 0005$ (dilute aqueous solution)
h=109±1 nm (close to $\lambda/4n_1$)

the reflection coefficient $R_0$ of the interface in the absence of ligands and receptors, that is when there is only the thin $SiO_2$ dielectric layer between the substrate and the solution, is less than $5 \cdot 10^{-6}$, In this case $R_0$ is markedly declined compared to the case where the dielectric layer is not present. In fact, in the latter condition, the reflection coefficient of the interface substrate-solution is about $8 \cdot 10^{-3}$.

Assuming that the thickness of the molecular layer of adsorbed or immobilized receptors and interacting ligands is less than 10 nanometers and the refractive indices of the molecules of receptor and ligand are equal, and have value $n_2$, the reflection coefficient R of the surface can be expressed using the following approximate formula, with an error less than 1% from the exact expression:

$$R = R_0 + \left[\sqrt{R_1 - R_0} + \frac{4\pi n_3}{\lambda \rho}\left(\frac{n_2 - n_3}{n_2 + n_3}\right)\left(\frac{M}{A}\right)\right]^2 \quad (2)$$

Where:

$R_0$, $\lambda$, $n_2$ and $n_3$ are as defined above, $R_1$ is the reflection coefficient (or reflectivity) of the interface measured following the procedure of immobilization of the receptor (a phase), M and $\rho$ are the mass and density of ligand, A is the surface area of solid material on which the adhesion of the receptor and ligand takes place.

Since the other physical quantities appearing in equations (1) and (2) are generally known or independently measurable, from the measure of the reflected intensity it is possible to extract the mass M of ligands interacting with the receptor via the above formulas.

For example, for the following parameters values:
$R_0 = 5 \cdot 10^{-6}$
$R_1 = 7 \cdot 10^{-6}$
$\rho = 1.15$ g/cm$^3$ (biomolecule, representative value)
$n_2 = 1.42$ (biomolecule, representative value)

the fractional change of the reflection coefficient, and hence the intensity of reflected light, due to the interaction between ligand and receptor is greater than 30% for M/A=1 ng/mm$^2$ and it is about 3% for M/A=100 pg/mm$^2$.

It should be noted that equation (2), which predicts an increase in the reflectivity when the amount of ligand present at the interface increases, is valid under the assumption that the wavelength $\lambda$ of the light is very close the value $4hn_1$, where, as defined above, h and $n_1$ are the thickness and refractive index of the dielectric layer, respectively. Otherwise, if the value of $\lambda$ is greater than $4hn_j$, in particular if $\lambda > 4(hn_1 + dn_2)$, where d and $n_2$ are the thickness and the refractive index of the functionalization layer including the receptor molecules, respectively, the interaction between ligands and receptors can lead to a decrease of reflectivity. Also in this case, the measure of the variation of the reflectivity allows the detection of the interaction between ligands and receptors, according to the present invention. Similarly to the above example, the said decrease of reflectivity is directly related to the mass of ligands interacting with receptors and the amount of interacting ligands can be computed through the thin layer Fresnel formulas from the measured decrease of the reflectivity.

The measurement of the mass of molecules with the function of ligand that interact with receptors immobilized on the surface, carried out as above described, can in turn determine the presence of ligand molecules in solution and, possibly, its quantity or its concentration, hence allowing the determination of the affinity constant K, also known as the binding constant between ligand and receptor, or the rate constants of association and dissociation.

In particular, the amount of ligand bound to the receptor at the equilibrium is expressed by a formula known as "Langmuir isotherm", which depends on the amount of receptors and the affinity constant K. For the Langmuir isotherm see, for example, PC Hiemenez and R. Rajaglopalan, "Principles of Colloid and Surface Chemistry, Marcel Dekker, New York, 1997, pages 287-298. If the affinity constant K of the specific ligand-receptor pair is known, the measurement of the mass balance of ligands immobilized on the surface allows to derive the concentration of ligand in solution. Otherwise, if the concentration of ligand in solution is known, the measurement of the mass balance of ligands immobilized on the surface allows to derive the value of the affinity constant K between receptor and ligand.

Alternatively, the diagram as a function of time of the amount of ligand immobilized on the surface can be used to derive the rate constants of association and dissociation, whose ratio provides the affinity constant K of the ligand-receptor pair. This procedure, commonly used in different label-free methods such as, for example, those based on SPR, is described, for example, in the book Rebecca L. Rich and David G. Myszka, "Extracting kinetic rate constants from binding responses", in "Label-free biosensors, techniques and applications", edited by Matthew A. Cooper, Cambridge University Press, 2009, pages 85-109.

The method of the present invention is applicable to transparent solutions, as well as turbid and/or absorbent, in agreement with the relation expressed in equation (1). In fact, the detected light signal comes exclusively from the specular reflection that occurs at the interface between the solution and the substrate, and is not affected by absorption or scattering of light occurring when light passes through the solution. Moreover, the method of the present invention is applicable to any angle of incidence, any polarization state, any degree of collimation and spectral composition of incident light, since for each of these variants the thicknesses and the refractive indices of the dielectric antireflective layers are selected in order to obtain a reflectivity less than 0.01%.

The dielectric material constituting the antireflective layer or layers can be, for example, silicon dioxide ($SiO_2$) deposited by vacuum evaporation (for example, "sputtering"). The surface, functionalized as described in step a), may be included in a cell for measurements in the absence of flow, or it may be included in a measuring cell that has the ability to flow the solution, or it may be included in an immersion probe.

The molecules or molecular complexes with the function of receptor that are used may be adsorbed or immobilized through different mechanisms. The adsorption may be due to electrostatic or hydrophobic interactions between the receptor molecules, possibly modified, and the solid surface, or between molecules and a layer of receptor molecules previously adsorbed or immobilized on the surface. The immobilization may be due to direct adsorption of receptor molecules, or the formation of covalent chemical bonds with dielectric material constituting the last layer of reflective coating (eg, using treatments with alkoxysilanes and their derivatives) or the formation of bonds with molecules or polymers (eg poly-lysine) previously adsorbed on the dielectric material. The molecules or molecular complexes with the function of receptors may be immobilized and/or chemically altered by prior art methods such as chemical methods, or electromagnetic radiation methods, or plasma treatment methods.

The molecules or molecular complexes with the function of ligand, after being immobilized on the surface due to interaction with receptors, may themselves act as a receptor for other molecules or molecular complexes with which they interact.

The receptor molecules, as mentioned, can be used in combination with molecules without the function of receptors (spacers). These molecules may be chosen for example between surfactants, carbohydrates, proteins and synthetic polymers or other molecules that have a limited interaction with the ligands in solution. This limited interaction can be verified by making the step (a) according to the method of the invention using only the spacer molecules without receptors and by checking that in step (b) no significant change in the intensity of reflected light is observed.

The ligand-receptor couple is defined as a couple of molecules, for example proteins, nucleic acids, glycoproteins, carbohydrates, hormones having an affinity capable of forming a more or less stable bond. In particular antibody/antigen, enzyme/inhibitor, carbohydrate/carbohydrate, protein/DNA, DNA/DNA, peptide/peptide couples can be mentioned.

In steps (a) and (b) of the method according to the invention, the measurements of the reflected light intensities are carried out by detecting the intensity of the reflected light, at more or less regular intervals of time, for example of 10 millisecond or longer, until reaching a constant value.

The change in the reflected light intensity can be caused by different physical phenomena. For example, the binding of ligands to receptors can cause a change in the optical path length associated with the dielectric layers. Alternatively, the binding can cause a change in refractive index or in the light absorption properties of the material that constitutes one of the dielectric layers. Said binding may also cause a swelling of the layer of receptor molecules, or of an underneath layer, resulting in a change in reflectivity.

The method of the present invention can simultaneously detect different type of receptor-ligand interactions with a limit of detection of about 10 picograms of ligand on a surface of 1 $mm^2$, using low-cost components, such as LED light sources and CCD or CMOS detectors, and without intrinsic limits on the minimum concentration in solution. The minimum detectable ligand concentration depends directly on the binding constant of specific receptor-ligand couple. Said limit of detection is comparable with that of the most sensitive techniques of the prior art.

The measurement surface is defined as the surface on which the receptor is bound or immobilized. The area of this region can be reduced to a value of few hundred of microns squared (corresponding for example to the area of a circular region with a diameter of a few tens of microns), thus allowing the detection of fractions of a picogram of ligand. The sensing surface of measurement can present several small measurement surfaces, where different receptors are adsorbed or immobilized. In this case, the method of the present invention can be used to identify and measure simultaneously, with measures of the reflected light intensity, the interaction of ligands in solution with different receptors in different locations of the low reflectivity surface. In particular, it is possible to immobilize different molecules with the function of receptor in different areas (spots) arranged in a matrix on the surface. The intensity of light reflected from the interface can then be detected by an imaging system (eg, via a digital camera), allowing simultaneous measurement of the intensity reflected from different spots and the intensity reflected from regions without receptors, outside of the spot, that can be used as a reference for the reflectivity signal.

The method of the present invention is based on the adhesion or immobilization on a surface, whose reflectivity is made low by one or more anti-reflective dielectric layers, of molecules (receptors) that expose to an aqueous solution a chemical group able to bind other molecules in solution (ligands). The measure of the increase or the amount of ligands interacting with receptors in response to flow at the surface of various molecular solutions, is a method for:

Detecting the presence within the fluid of molecules (ligands) that bind the molecules of the first layer;
Screening of ligand molecules mixed with other chemicals;
The measure of the amount of bound ligands as function of the concentration of ligands in solution, and through it,
The measure of the affinity constant ligand-receptor interaction;
The measure of the amount of bound ligands as a function of time, and through it,
The measure of the constants of association and dissociation.

It is surprising that the reflection of light from a surface coated with one or more anti-reflective dielectric layers turned out to be effective in identifying and measuring directly, through measurement of reflected light intensity, the interactions between receptors and ligands according to the method of the present invention.

Some examples follow with illustrative but not limitative purposes of the present invention.

EXAMPLES

Example 1

Simultaneous Detection of the Interaction Between Antibodies in Solution and Proteins Immobilized in Different Areas Using an Image Acquisition System A layer of 109 nm of silicon oxide ($SiO_2$) was deposed by sputtering on one side of a prism made by Schott N-SK5 glass, forming an angle of 5° with the opposite side. The thickness of the dielectric layer and the substrate are chosen so as to greatly reduce the reflectivity of the surface when it is in contact with an aqueous medium, under conditions of normal incidence of monochromatic light of wavelength 632.8 nm.

BRIEF DESCRIPTION OF THE DRAWINGS

The prism is inserted in a flow cell so that the treated surface (hereinafter called "sensing surface") is in contact with the aqueous solution. FIG. 1 shows a schematic drawing of a section of the assembled cell. The cell is constructed in such a way that it does not exhibit any flat surface parallel to the sensing surface. This is done in order to facilitate the selection, according to the direction of propagation, of the light reflected from the sensing surface.

In FIG. 2 is represented schematically, not in scale, the illumination system and collection system used for the execution of the experiment. The light from a red LED with peak wavelength of 636 nm is collimated and shaped by a system of diaphragms and lenses (according to the scheme of Köhler illumination) to provide on the sensing surface plane an even illumination, with limited angular divergence. With the help of a semi-reflective mirror (beam splitter) the light reflected from the sensing area is collected by a lens which forms an image of the sensing surface on the sensor plane of a CCD camera connected to a computer.

A diaphragm placed in the back focal plane of the collection lens allows to select only the light reflected from the interface of interest, blocking most of the light rays reflected by other surfaces of the cell. In this way the light that contributes to the formation of the image of the sensing surface comes almost exclusively from the specular reflection from the sensing surface itself and the intensity measured by each element of the CCD sensor is directly linked to the surface density of adsorbed mass in the corresponding region of the sensing surface according to equation (1).

On the sensing surface of the prism are deposited with a pipette two droplets, of about 0.1 microliters in volume, about 2 millimeters apart. The first drop consists of an aqueous solution containing sodium phosphate buffer pH 7.4+150 millimolar NaCl (hereafter called "phosphate buffer") and protein avidin (marketed by Sigma-Aldrich, prod. No. A9275) at a concentration of 3 micromolar. The second drop is composed of a solution containing phosphate buffer, protein concentration of 3 micromolar of avidin and biotin at a concentration of 6 micromolar. This second solution was prepared 30 minutes before the deposition of drops. According to the high avidin-biotin binding constant and to the molar ratio of the two reagents, it is expected that at the time of deposition of the droplets, approximately half of the binding sites of Avidin molecules are free.

After about 10 minutes from the deposition the prism is inserted into the flow cell and the drops are removed from the surface by flowing through the cell for about 30 minutes a solution of phosphate buffer at a flow rate of 10 microliters per minute.

This procedure is intended to produce on the sensing surface two regions ("spots") coated with a layer of avidin protein.

In spot (1), created by the first drop, there is avidin protein, in the spot (2), created on the second drop, there is avidin protein with about half of its binding sites left free. During the experiment are flowed into the cell with a constant flow rate of 10 microliters/minute, the following solutions:
a) phosphate buffer for a total volume of 300 microliters;
b) phosphate buffer containing protein bovine serum albumin, BSA conjugated to biotin (marketed by Sigma-Aldrich, prod. No. A8549) at a concentration of 0.5 micromolar for a total volume of 100 microliters;
c) phosphate buffer for a total volume of 300 microliters;
d) antibody anti-BSA (marketed by Sigma-Aldrich, prod. No. B 1520) at a concentration of 0.1 micromolar for a total volume of 100 microliters;
e) phosphate buffer for a total volume of 300 microliters.

For the whole duration of the experiment every 5 seconds a digital image of the sensing surface is acquired through the camera and the image is saved on the hard disk of the computer connected to the camera.

Figure 1:
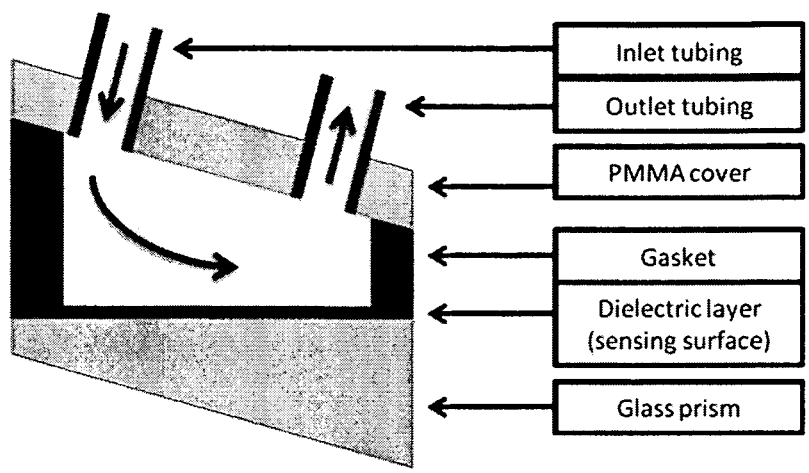
FIG. 1 illustrates a schematic drawing of a section of the assembled cell.
Figure 2:
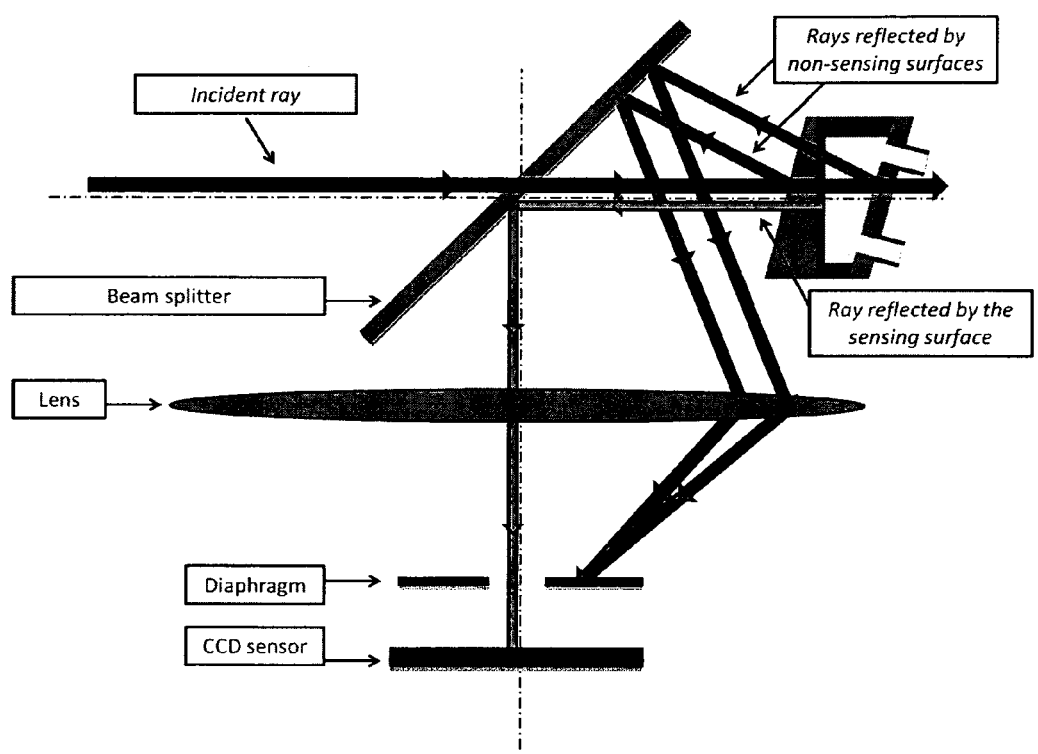
FIG. 2 schematically illustrates the illumination system and collection system used the experiment.
Figure 3:
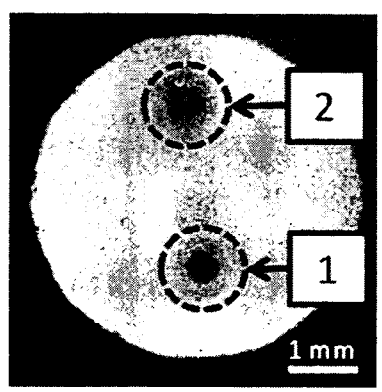
FIG. 3 shows an image acquired during the measurement phase of the experiment.

FIG. 3 shows an image acquired during the measurement. There are marked with dashed circles the regions where the two droplets have been deposited. For each image, the average gray level (average brightness) of the portion of the image corresponding to each spot is calculated. The brightness of each spot versus time is shown in the upper portion of FIG. 4 (black points: spot 1, light gray points: spot 2).

It is noted that during step (b) of the experiment the brightness of spot 1 decreased more markedly than spot 2. This change in brightness is attributed to the formation of Avidin-Biotin bonds between molecules immobilized and BSA conjugated to biotin molecules present in solution. The same behavior is observed during step (d) where the change in brightness is attributed to bond formation between the BSA on the surface and the specific antibody present in solution. It is observed that the molecular adhesion on the surface leads to a decrease in the intensity of the reflected light. This is due to the fact that the light from the LED lamp has a peak wavelength greater than 633 nanometers, which is the wavelength that minimizes the reflectivity of the surface.

Figure 4:
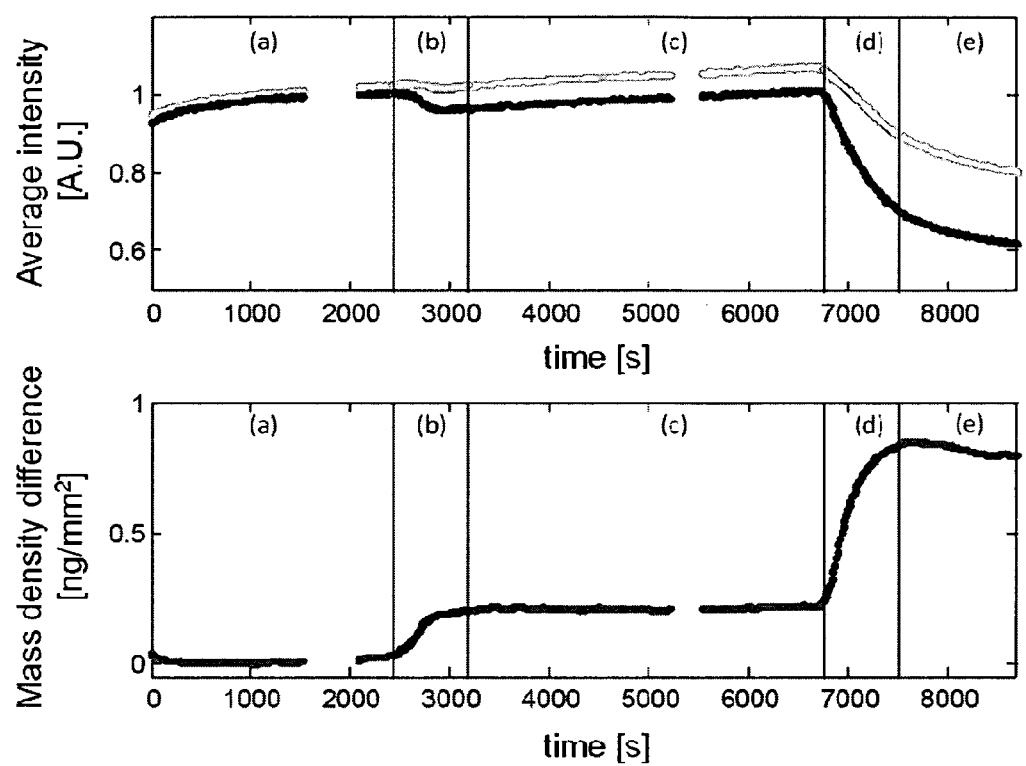
FIG. 4 shows the time evolution of the difference between the mass surface density in the two spot, calculated using the equation (2)

The lower portion of FIG. 4 shows the time evolution of the difference between the mass surface density in the two spot, calculated using equation (2). This reduces the spurious drift of the signal that can be observed in particular during steps a) and c).

Example 2

Detection of the Interaction Between Antibodies and Immobilized Proteins in Solution Using a Laser Source A layer of silicon oxide ($SiO_2$) was deposed by sputtering on one side of a glass prism, as described in Example 1. The prism is placed in a flow cell so that the coated surface is in contact with the aqueous solution. A light beam from a 5 milliwatts He—Ne laser is sent to the interface between the aqueous solution and the prism and the reflected light is detected by a photodiode that converts the light intensity in an electrical signal. Through the cell is promoted a flow of 10 microliters/minute of an aqueous solution containing sodium phosphate buffer pH 7.4+150 millimolar NaCl (hereafter called "phosphate buffer") in the following order:
a) phosphate buffer
b) protein Avidin (marketed by Sigma-Aldrich, prod. No. A9275) at a concentration of 3 micromolar;
c) phosphate buffer;
d) protein Bovine Serum Albumin, BSA (marketed by Sigma-Aldrich, prod. No. A6003) at a concentration of 0.4 micromolar;
e) phosphate buffer;
f) protein BSA conjugated to biotin (marketed by Sigma-Aldrich, prod. No. A8549) at a concentration of 0.5 micromolar;
g) phosphate buffer;
h) antibody anti-BSA (marketed by Sigma-Aldrich, prod. No. B 1520) at a concentration of 0.1 micromolar;
i) phosphate buffer.

Figure 5:
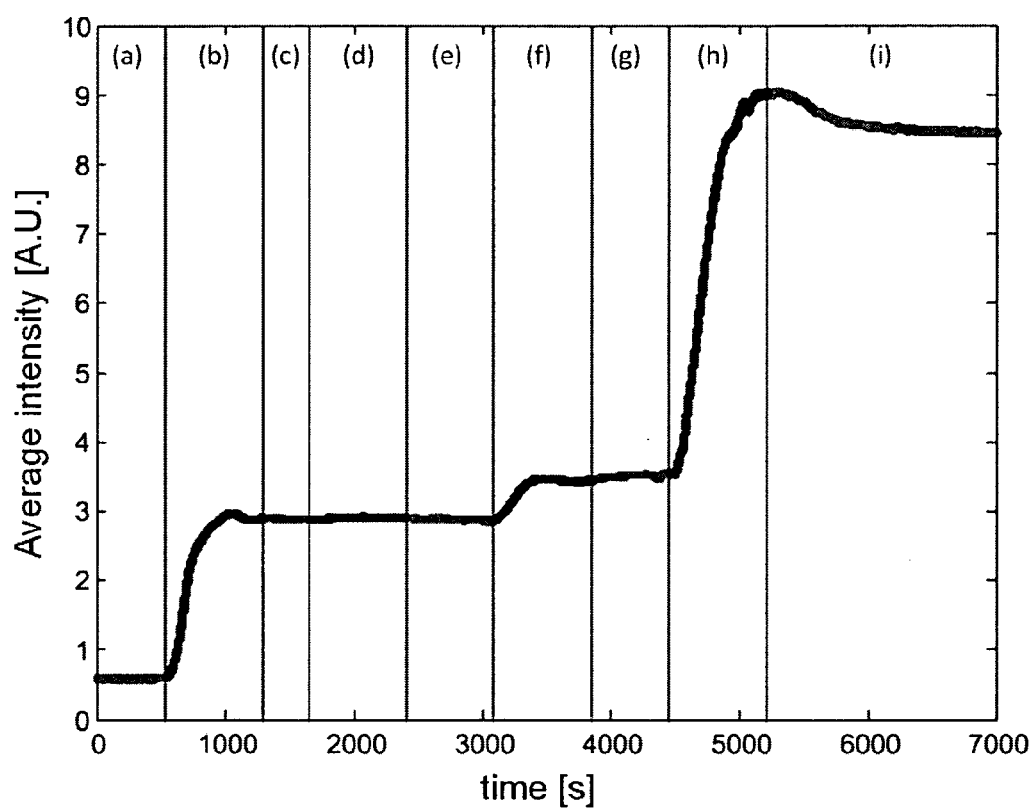
FIG. 5 is a graphical representation of the measured reflected intensity as a function of time.

In FIG. 5 the measured reflected intensity is reported as a function of time. The value of the reflected light intensity measured before the step a) corresponds to a reflectivity of $3.2 \cdot 10^{-6}$. After the increase in the reflected intensity due the adsorption of Avidin protein on the surface active (a), no further variation is observed when in the cell is flowing the solution containing BSA protein (c), while an increase is observed when the solution containing BSA protein conjugated with biotin is flowing (e). This shows that the measure of reflected intensity is indicative of the specific interaction between Biotin and Avidin. In correspondence with the solution containing anti-BSA (g) we observe a further increase in signal intensity reflected that indicates an interaction between the antibody and the BSA immobilized. Unlike in Example 1, in this case the adhesion molecules on the surface causes an increase in the intensity of reflected light. This is due to the fact that the laser radiation used has a wavelength of 632.8 nanometers, which is precisely the wavelength for which there is minimum reflectivity of the surface.

The invention claimed is:

1. A method for detecting and/or quantifying ligand-receptor binding between a ligand in solution and a receptor for said ligand immobilized on a solid surface, comprising the following steps:
a) coating a surface of a substrate of a solid crystalline or amorphous material with one or more dielectric layers of thickness between 50 nm and 500 nm, wherein the surface has a reflectivity, when in contact with an aqueous solution, of less than 0.01%;

b) immobilizing the receptor molecules on said coated surface;

c) contacting said surface carrying the immobilized receptors with a solution containing the ligands;

d) illuminating the substrate with light of wavelength λ; and e) measuring the light intensity reflected at wavelength λ from an interface between the solution and the surface carrying the immobilized receptors as a function of time, and converting the measured values of reflected light intensity into values of mass per surface unit of ligand molecules bound to the receptors, utilizing Fresnel formulas for thin layer reflection.

2. The method according to claim 1, wherein the value of reflected light intensity or the value of mass per surface unit of ligand molecules bound to the receptors, as measured in step e), are further converted into total quantity or concentration of ligand molecules in the solution.

3. The method according to claim 1, further comprising converting the value of reflected light intensity or the value of mass per surface unit of ligand molecules bound to the receptors, as measured in step e), into a ligand-receptor affinity constant.

4. The method according to claim 1, further comprising converting the values of the reflected light intensity as a function of time, as measured in step e), into association and/or dissociation kinetic constants of the ligand-receptor pair.

5. The method according to claim 1, wherein said substrate of a solid crystalline or amorphous material has a refractive index between 1.4 and 1.7.

6. The method according to claim 5, wherein said amorphous material is siliceous glass.

7. The method according to claim 1, wherein the one or more dielectric layers have a refractive index greater than 1.35.

8. The method according to claim 1, wherein
said coated surface is divided into different areas, optionally arranged as an array,
different receptors are adsorbed or immobilized on the different areas, and
the reflected light intensity from the different areas is simultaneously measured by an imaging system.

9. The method according to claim 1, wherein the receptors are immobilized on the surface through spacer molecules.

10. The method according to claim 1, wherein the ligand-receptor pair comprises proteins, peptides, nucleic acids, glycoproteins, carbohydrates, hormones, lipids, cells, cellular components, virus or molecules of pharmacological interest.

11. The method according to claim 1, wherein the receptors are immobilized on the surface through:
a. chemical bonding;
b. adsorption;
c. adsorption on molecules or polymers previously immobilized on the surface;
d. electromagnetic irradiation; or
e. plasma treatment.

12. The method according to claim 1, wherein the solution containing the ligands and in contact with said surface carrying the immobilized receptors is not an aqueous solution.

13. The method according to claim 1, wherein optical filters are used to reduce angular spread or spectral width of incident light, or to select a linear polarization of collected light, in order to maximize the ratio between the reflected light signal in the presence of ligand-receptor binding and a background signal due to other light reflections and scattering for a given angle of incidence.

14. The method according to claim 1, wherein said surface with the immobilized receptors is embodied in a non-flow cell, in a flow cell, or in an immersion probe.

15. The method according to claim 1, wherein the reflected light intensity is measured by illuminating the substrate with light from an LED source and measuring the reflected light intensity with an image sensor.

16. The method according to claim 15, wherein the image sensor is a CCD or a CMOS detector.

17. The method according to claim 15, wherein the light from the LED source illuminating the surface is collimated and shaped by one or more diaphragms and lenses and the reflected light to be measured is collected with one or more beam splitters and lenses.

18. The method according to claim 1, wherein the reflected light intensity is measured by illuminating the surface with light from a laser source and measuring the reflected light with a photodiode.

19. A method for detecting and/or quantifying ligand-receptor binding between a ligand and a receptor for said ligand, comprising:

a) providing a substrate of a solid crystalline or amorphous material, the substrate having a surface coated with one or more dielectric layers of thickness between 50 nm and 500 nm,
wherein the dielectric coated surface has a reflectivity, when in contact with an aqueous solution, of less than 0.01%,
said receptors being immobilized on a surface of said one or more dielectric layers;

b) contacting said surface carrying the immobilized receptors with a solution containing the ligand;

c) illuminating the substrate with light of wavelength λ;

d) measuring the reflected light intensity at wavelength λ from an interface between the solution and said surface carrying the immobilized receptors as a function of time; and e) converting the measured values of reflected light intensity into values of mass per surface unit of ligand molecules bound to the receptors, utilizing Fresnel formulas for thin layer reflection.

20. The method according to claim 19, wherein the measured values of reflected light intensity are converted into values of mass per surface unit of ligand molecules interacting with the receptors according to the formula:

$$R = R_0 + \left[ \sqrt{R_1 - R_0} + \frac{4\pi n_3}{\lambda \rho} \left( \frac{n_2 - n_3}{n_2 + n_3} \right) \left( \frac{M}{A} \right) \right]^2$$

wherein,
R is the reflection coefficient obtained from a Fresnel formula for a stratified dielectric media, depending on the amount of ligand in contact at any given time with the receptors immobilized on the surface,
$R_0$ is the reflection coefficient of the interface in the absence of ligand and receptor,
$R_1$ is the reflection coefficient of the interface in the presence of immobilized receptor,
$n_2$ is the refractive index of the receptor and ligand,
$n_3$ is the refractive index of the solution,
λ is the wavelength of light illuminating the substrate, A is the surface area of the surface carrying the immobilized receptors in contact with the solution containing the ligand, and M and $\rho$ are the mass and density of ligand.

* * * * *